(12) United States Patent
Kantor et al.

(10) Patent No.: US 9,706,929 B2
(45) Date of Patent: Jul. 18, 2017

(54) METHOD AND APPARATUS FOR IMAGING TISSUE TOPOGRAPHY

(71) Applicant: The Provost, Fellows and Scholars of the College of the Holy and Undivided Trinity of Queen Elizabeth Ne, Dublin (IE)

(72) Inventors: Roman Kantor, Dublin (IE); Guido Mariotto, Dublin (IE); Igor Shvets, Dublin (IE)

(73) Assignee: The Provost Fellows and Scholars of the College of the Holy and Undivided Trinity of Queen Elizabeth, Near Dublin, Dublin (IE)

( * ) Notice: Subject to any disclaimer, the term of this patent is extended or adjusted under 35 U.S.C. 154(b) by 0 days.

(21) Appl. No.: 15/078,714

(22) Filed: Mar. 23, 2016

(65) Prior Publication Data

US 2016/0270665 A1    Sep. 22, 2016

Related U.S. Application Data (63) Continuation of application No. 13/203,005, filed as application No. PCT/EP2010/001168 on Feb. 25, 2010, now abandoned.

(Continued)

(30) Foreign Application Priority Data

Feb. 25, 2009   (EP) .................................. 09153655

(51) Int. Cl.
*A61B 5/00*   (2006.01)
*G06T 7/00*   (2017.01)
(Continued)

(52) U.S. Cl.
CPC .......... *A61B 5/0077* (2013.01); *A61B 5/0059* (2013.01); *A61B 5/0075* (2013.01);
(Continued)

(58) Field of Classification Search
None
See application file for complete search history.

(56) References Cited

U.S. PATENT DOCUMENTS

| 5,198,875 A | 3/1993 | Bazin et al. |
| 5,836,872 A | 11/1998 | Kenet et al. |

(Continued)

FOREIGN PATENT DOCUMENTS

| DE | WO 2008125605 A2 * | 10/2008 | ......... G01B 11/2504 |
| EP | 1814083 A1 | 8/2007 | |

(Continued)

OTHER PUBLICATIONS

PCT Written Opinion for International Patent Application No. PCT/EP2010/001168, mailed Aug. 30, 2011, 11 pgs.

*Primary Examiner* — Mohammad J Rahman
(74) *Attorney, Agent, or Firm* — K&L Gates LLP (57) ABSTRACT

The present invention relates to an optical device for imaging and measuring characteristics of an objects surface shape, surface spectral reflectance and structure of sub-surface layers. In particular, the invention relates to imaging of topography of human skin and skin sub-surface layers and determination of concentration of skin constituents. The present invention has applications in areas such as skin care, dermatology, cosmetics, wound management and tricology. The imaging device of the invention significantly improves photometric stereo measurements by suppressing specular reflection and allows accurate determination of the surface shape. Consequently the device allows elimination of the influence of the shape and illumination conditions on spec- (Continued)

tral measurements and allows accurate measurement of skin constituents.

22 Claims, 7 Drawing Sheets

Related U.S. Application Data (60) Provisional application No. 61/155,442, filed on Feb. 25, 2009.

(51) Int. Cl.
- *G06K 9/62* (2006.01)
- *A61B 5/145* (2006.01)
- *G06T 7/586* (2017.01)

(52) U.S. Cl.
CPC .......... *A61B 5/14546* (2013.01); *A61B 5/442* (2013.01); *A61B 5/443* (2013.01); *A61B 5/444* (2013.01); *A61B 5/445* (2013.01); *A61B 5/7203* (2013.01); *G06K 9/6215* (2013.01); *G06T 7/0012* (2013.01); *G06T 7/586* (2017.01); *A61B 2560/0223* (2013.01); *A61B 2562/08* (2013.01); *G06T 2207/10152* (2013.01); *G06T 2207/30024* (2013.01); *G06T 2207/30088* (2013.01)

(56) References Cited

U.S. PATENT DOCUMENTS

| | | | |
|---|---|---|---|
| 6,686,921 B1 | 2/2004 | Rushmeier et al. | |
| 7,539,330 B2 * | 5/2009 | Rowe | G06K 9/00046 340/5.53 |
| 8,026,942 B2 | 9/2011 | Payonk et al. | |
| 2002/0042559 A1 * | 4/2002 | Buschmann | A61B 5/1464 600/331 |
| 2003/0015649 A1 | 1/2003 | Levecq et al. | |
| 2005/0273011 A1 | 12/2005 | Hattery et al. | |
| 2006/0058683 A1 | 3/2006 | Chance | |
| 2006/0092315 A1 | 5/2006 | Payonk et al. | |
| 2006/0178570 A1 | 8/2006 | Robinson et al. | |
| 2006/0239547 A1 | 10/2006 | Robinson et al. | |
| 2007/0080223 A1 | 4/2007 | Japuntich | |
| 2007/0146702 A1 * | 6/2007 | Canning, Jr. | G01N 1/2813 356/336 |
| 2007/0176927 A1 | 8/2007 | Kato et al. | |
| 2009/0004757 A1 * | 1/2009 | Yguerabide | C12Q 1/6816 436/501 |
| 2009/0079937 A1 | 3/2009 | Chen et al. | |
| 2009/0245603 A1 | 10/2009 | Koruga et al. | |
| 2010/0108873 A1 * | 5/2010 | Schwertner | G01B 11/2504 250/252.1 |
| 2011/0184260 A1 | 7/2011 | Robinson et al. | |
| 2012/0321759 A1 | 12/2012 | Marinkovich et al. | |
| 2014/0012140 A1 | 1/2014 | Freeman et al. | |
| 2014/0303463 A1 | 10/2014 | Robinson et al. | |

FOREIGN PATENT DOCUMENTS

| | | |
|---|---|---|
| FR | 2821152 | 8/2002 |
| WO | 9616698 A2 | 6/1996 |

\* cited by examiner

Figure 7a: 3D representation of the skin with natural colour texture

Figure 7b: 3D representation of the skin devoid of the texture under directional illumination Figure 7c: 3D representation of the skin with visualisation of small roughness (wrinkles)

Figure 7d: 3D representation of the skin with visualisation of melanin concentration Figure 7e: 3D representation of the skin with visualisation of haemoglobin concentration

METHOD AND APPARATUS FOR IMAGING TISSUE TOPOGRAPHY

CROSS REFERENCE TO RELATED APPLICATIONS

This application is a continuation of U.S. Nonprovisional application Ser. No. 13/203,005, filed on Aug. 24, 2011, which is a national phase application under 35 U.S.C. §371 of International Application No. PCT/EP2010/001168, filed on Feb. 25, 2010, which claims priority to and the benefit of U.S. Provisional Patent Application No. 61/155,442, filed on Feb. 25, 2009 and European Patent Application No. 09153655.7, filed on Feb. 25, 2009, the entire disclosures of each of which are incorporated by reference herein.

FIELD OF THE INVENTION

The present invention relates to an optical apparatus and method for imaging and measuring characteristics of a surface. In particular, the invention relates to imaging of topography of human skin tissue and skin sub-surface layers and determination of concentration of skin constituents.

BACKGROUND TO THE INVENTION

Improving physical appearance of humans has become a significant social priority in many countries, which explains the continuous rise in popularity of cosmetic products and skin care treatments. The skin care market is continuously growing, driven by a demand for customised products and by customers who are ready to pay for quantifying the results of their treatments by means of more and more sophisticated instruments. This has resulted in the development of in-vivo scanners for the analysis of skin. As opposed to the conventional methods of using a silicone rubber replica to examine the skin's topography, in-vivo scanners have the advantage of being less invasive and less prone to artefacts, for example as disclosed by J. Hatzis, Micron 35 (2004), 201-219.

A variety of in-vivo scanners are available on the market, employing a variety of techniques to acquire the images of the skin surface. One such scanner is manufactured by Moritex Corporation and described in U.S. Pat. No. 6,118,476. This instrument includes two polarised illumination systems having polarisation directions perpendicular to each other, and an analyser disposed on an optical path from the object to a CCD device. The analyser has a vibrating direction parallel to one of the illumination systems and perpendicular to the other one. The illumination system whose polarisation direction is parallel to the one of the analyser is sensitive to the surface state of the object, while the system whose polarisation is perpendicular to the one of the analyser provides information on the sub-surface layer. More recently, Moritex Corporation has patented another system in the US consisting of a main body and a detachable head and granted under number U.S. Pat. No. 7,151,956. An illumination light source (in the form of white LEDs) is placed in the main body together with an imaging apparatus. The detachable head is provided with optical fibres for guiding light from the illumination source to the object being imaged. Because optical fibres are much thinner than LEDs, according to the inventors, a more homogeneous illumination of the object can be achieved.

A device for measuring skin parameters similar to the one manufactured by 'Courage+Khazaka electronic GmbH' is described in U.S. Pat. No. 6,251,070. The apparatus consists of a casing containing optical recording means and light emitting means connected to a light source (a neon light tube). The aim of this patent is to increase the contrast of the images acquired by using light in a wavelength range between 350 and 400 nm. The instrument also provides means to measuring the level of humidity and sebum of the skin by means of a replaceable film placed at a distance from the optics. This film, initially opaque, becomes transparent as it absorbs the skin's secretions.

In U.S. Pat. No. 6,571,003, a method and apparatus for analysing a plurality of visual skin defects is described. In this US patent, the image acquisition system consists of a conventional digital camera. The digital image acquired is electronically analysed and defect areas are located. Subsequently, the system displays a second digital image, based on the first acquired digital image, identifying the defect areas by electronically altering the colour of a plurality of pixels corresponding to the skin defects.

In U.S. Pat. No. 6,907,193, the skin of a person is imaged by illuminating the skin with at least one light source, where the light emitted from the source is filtered using a polariser. The image is captured using a camera in a way that the angle formed by the light source, the skin, and the camera is from about 35 degrees to about 55 degrees. This arrangement is utilised to minimise the surface glare from the skin surface.

A hand-held device developed for dermatoscopy applications is described in U.S. Pat. No. 7,006,223. This device consists of two concentric rings of LEDs and a magnifying lens, through which the user views the patient's skin. A special arrangement of two polarisers allows switching between parallel-polarized and cross-polarized images to aid viewing internal structures as well as the skin surface.

All the techniques employed in the patents described above, image the skin surface in two dimensions. However it is preferable to provide images of the skin surface in three dimensions. Several techniques deal with the problem of recovering the three-dimensional shape of a surface known in the art. For example, the 'binocular stereo' technique is based on the acquisition of two images taken from different viewpoints. The depth of the surface is recovered by identifying corresponding points in the two images. This method has been successfully applied in cartography, but it suffers from several drawbacks. The main one is the determination of the corresponding features between two separate images, taken from different points of view. This requires the implementation of matching algorithms that result in additional complex computation.

U.S. Pat. No. 6,263,233 makes use of three-dimensional techniques for imaging the skin surface. A handheld microscope for the imaging of dermal and sub-dermal tissue is described. This instrument is based on the principle of 'confocal microscopy', and allows scanning the tissue at successive depths to provide images of vertical sections. By combining the optical slices, a three dimensional image of the tissue can be obtained.

'Shape from shading' (SFS) is a technique that computes the three-dimensional shape of a surface from the intensity variation in one image of that surface. SFS technique was proposed by B. K. Horn, The Psychology of Computer Vision, P. H. Winston ed., New York, 1975. Since describing surface orientation requires two variables, and measurements of brightness at a single point in the image provide only one variable, the problem of image reconstruction cannot be solved unless further assumptions are made. The assumptions made usually comprise knowing exactly the lighting condition and the surface reflectivity, as well as assuming that the surface is smooth and has a homogeneous texture. Furthermore, even if all these conditions are satisfied, the surface gradient cannot be uniquely determined for every pixel.

Figure 1:
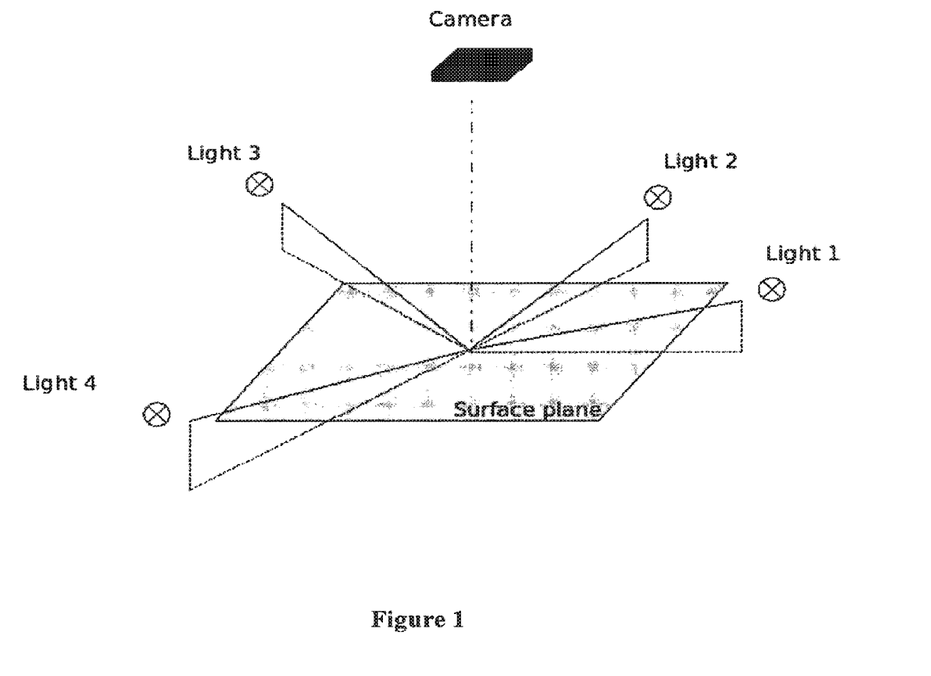
FIG. 1 is an illustration of photometric stereo geometry.

'Photometric stereo' was first proposed by Woodham, Optical Engineering 19 (1980) 139-144, and consists of varying the direction of incident illumination between successive images, while holding the viewing direction constant and taking at least two images for at least two different illumination directions. Woodham showed that three images taken for different illuminations are sufficient to uniquely determine both the surface orientation and the reflectance factor at each image point. An illustration of photometric stereo geometry is given in FIG. 1. A computer-based analysis is then used to determine surface orientation at each image point, usually by defining normal vectors of the surface for all these points.

Most photometric stereo methods use a technique when a multiple subsequent image frames are acquired by a camera when illumination conditions are changed by synchronous switching on/off three or more light sources with different position and illumination angle so that for each frame one source is illuminating the surface. Such a system is also described by European patent Publication number EP 1 814 083, assigned to Omron Corporation. Unfortunately the disclosed configuration does not eliminate the specular reflection by any means of optical configuration nor by any compensation during data processing. This means that for used Lambertian reflection model the system can be successfully applied only on relatively limited set of surface types with low specular reflectivity. For most purposes and most practical surfaces with non-negligible specular reflection, the measured data and the results are affected by significant errors.

It is known to use polarisation optics in various fields of optical imaging. One possible use is described in US patent publication number US2006/0239547, Robinson et al. The application does not use photometric stereo methods or its measurement configuration, neither does it perform surface shape reconstruction. Secondly it uses different property of light polarization—the dependency of the propagation depth on the polarisation state: by tuning this polarisation it selects the depth of the sub-surface layers from which the scattered light is detected on the sensor. As such this US publication does not aim to produce accurate 3D profiles of a surface and the methods described there cannot be used for detailed specification of the object shape.

In the photometric stereo measurements one of the main constraints for the accurate calculation of the surface tilt from reflected intensities is the use of appropriate optical reflection model to relate measured reflected intensities with the tilt angles of the surface. As the optical model varies depending on the surface type, a simple Lambertian reflection model is usually used if the optical properties of the surface are unknown or vary across the object surface. Normally the techniques which rely on Lambertian reflection model are prone to the errors caused by specular reflection on not fully diffusive surfaces. Some techniques try to eliminate the influence of specular reflection by the use of more than three illumination sources and the data burden with high specular component are excluded from the calculation. Such data are usually identified as the data with the maximum intensity from the set of all acquired frames for each individual pixel of the detector.

H. Saito, Y. Somiya and S. Ozawa, ACCV'95, 3 (1995), 348-352 describes a method to reconstruct the 3D shape of a skin surface replica using a modification of the photometric stereo technique. As explained above, in the conventional photometric stereo technique the gradient of the surface is uniquely determined by inverse analysis from three reflectance values of the three different light sources. However, the gradient cannot be determined if three values are not available due to the effect of shadow. To cope with such cases, Saito et al. define the evaluation function of the surface shape in consideration of the effects of shadow, and then reconstruct the shape by optimizing the evaluation using simulated annealing (SA). In other words, the shape of the surface is estimated by the iteration process. In each iteration, the estimated shape is evaluated by comparing the estimated shading images, which are synthesized from the estimated shape in the consideration of the effect of the shadow. The technique was later extended by A. Matsumoto, H. Saito and S. Ozawa, Electrical Engineering in Japan, 129 (3), 1391

Some other methods for skin topography measurement, such as interference fringe projection, optical triangulation and autofocuss can be also found in the literature, for example, J. M. Lagarde C. Rouvrais, D. Black, S. Diridollou, Y. Gall, Skin Research and Technology 7 (2001), 112-121 and J. L. Leveque, Journal of European. Academy of Dermatology and Venereology, 12 (1999) 103-114. However, many of these methodologies are problematic due to complexity of the instrumentation used and spatial constrains for the object positioning.

Some skin inspection systems use a number of individual detectors or array of the detectors to acquire the light directed to different angles after the reflection from particular point of the surface. Such systems can also be combined with multiple illumination sources such as the above mentioned US Patent Publication number US2006/0239547. Although the systems described in this application also comprises a translation system to scan through the area of interest, it does not provide means for full reconstruction of the surface shape and it does not use photometric stereo method for the surface shape recovery. On the other hand it describes a possibility to measure overall surface change in a photo-cell like arrangement with the use of collimated light source and a linear array of the detectors. The skin elevation is measured by detecting a shadow projected to the detector array. The application also describes the use of polarized light to tune depth of light propagation under the skin surface. It also uses of different light colors to further specify properties of the skin.

The techniques described above have been used in the most diverse fields, ranging from cartography to face reconstruction, to medical applications such as the endoscopic image of the stomach. However, they have not found widespread use due to a number of technical problems especially due to the different optical properties of inspected objects data must be processed in a different way for each different application.

An object of the present invention is to devise a means and method for accurate real-time three-dimensional imaging of a tissue surface, by effective suppression of the influence of specular reflection.

A further object of the present invention is to devise a means and method for obtaining spectral characteristics of tissue surface combined with the capability to reconstruct the three-dimensional image of the surface. A further object of the invention is to devise means and method for imaging tissue surface under conditions of more uniform illumination across the imaged area.

SUMMARY OF THE INVENTION

According to the present invention there is provided, as set out in the appended claims, an image capture device, for example for the acquisition of the topography of a skin tissue surface, comprising:
- a plurality of illumination sources for illuminating said surface;
- an optical system adapted for the capture of a plurality of images of said surface;
- means for controlling said illumination sources and said optical system enabling changing spatial properties of the illumination such as illumination direction and capturing said plurality of images for different spatial properties of the illumination;
- means for eliminating specular reflection from said captured images wherein the means for eliminating said specular reflection comprises at least two polarisers, a first polariser positioned between the illumination sources and the surface, and a second polariser between the surface and the optical imaging system; and
- means for analysing the differences between images captured with different illumination properties to reconstruct the topography of said surface based on a diffusive reflection model.

The system and method of the invention facilitates three-dimensional imaging of partially diffusive or diffusive surfaces, and in particular human skin surfaces. The present invention utilizes the effect that light specularly reflected from a tissue surface does not change its polarization state, while light that undergoes diffusive reflection can change its polarization. By eliminating specular reflection can be suppressed. The system of the invention makes use of such polarisation filtering. Suppression of the specular reflection enables for the accurate analysis of the shape in photometric stereo based on the standard Lambertian reflection model.

For highly specular surfaces the above described method which uses the polarisers to suppress the specular reflection can be further combined with the use of specular data selection method Where the redundant data with significant residual specular reflection component are eliminated from the analysis. For the elimination method more than three images are required and the data burden with highest specular component are excluded from the calculation. Such data are usually identified as the data with the maximum intensity from the set of all acquired frames for each individual pixel of the detector. The data elimination method improves the accuracy of the results for certain surface types when the specular reflection occurs only within a narrow angle around the direction determined by equivalent-angle reflection law. For surfaces with broad specular reflection angles the specular reflection contributions may appear in multiple acquired data for multiple illumination directions but in this case such a contribution is usually of much lower intensity and can effectively suppressed by described cross-polarisation filtering. The combination of polarisation filtering and specular data elimination seems to be very effective method to reduce the influence specular reflection and instruments based on this combination can give accurate shape reconstruction of broad variety of surface types.

Having a high number of illumination sources increases the accuracy of the evaluation of the surface intensities and allows influence of surface self-shadowing to be limited. In all photometric stereo methods which use more than three illumination sources only one source is switched on at a time and illuminates the surface during particular single image acquisition. This prolongs the total acquisition times especially for large number of sources with lower intensities. According to another present invention, a number of individual sources can illuminate the surface at the same time during acquisition of a single image. This significantly reduces total acquisition time as not only lower number of images must be acquired but also camera exposition times can be much shorter as the illumination intensity increases when sources are combined. This is especially important for dynamic objects witch changing position or shape, such as skin tissue measurements, when all data need to be acquired during very short period during which the motion does not significantly change the object position relative to the image acquisition system. Normally combination of sources would bring difficulties for characterisation of such illumination. However the two or more sources can be characterised as single "virtual" source. If each individual source is characterised by an illumination vector having direction parallel to the light propagation and magnitude proportional to the light intensity, the combined source can be characterised as algebraic sum of individual source vectors. It should be appreciated that this sum is allowed only when using a linear Lambertian reflection model—which in the case of the present invention provides accurate results because it provides a means of eliminating of specular reflectivity.

In one embodiment the present invention provides a technique where crossed polarisers are used as the only method to suppress specular reflection. In such configuration no data need to be excluded from calculation thus accurate results can be obtained even using low number of light sources.

In one embodiment the first and second polarisers are linear light polarisers and aligned in a cross-polarised relationship with each other.

In one embodiment the plurality of captured images are of substantially the same area with varying illumination conditions all under the same polarisation direction of the incident light and substantially cross-polarised direction of detected reflected and scattered light.

In one embodiment the specular reflection suppression using polarisers is combined with the use of four or more illumination sources for the surface characterisation and further elimination of the data burden with remaining high specular component from the calculation. For each individual pixel of the detector, the data with high specular component is identified as the data with the maximum intensity from the set of all acquired frames.

In one embodiment two or more sources illuminate the object at a time to increase the illumination intensity and reduce the number of individual images acquired.

In one embodiment the means for analysing comprises processing said plurality of captured images to calculate the tilt of the surface at each point of the area from the difference between images taken under different illumination conditions and recover the topography of the surface.

In one embodiment at least one of the illumination sources operate within the visible range of the electromagnetic spectrum.

In one embodiment at least one of the illumination sources emits radiation outside the visible range of the electromagnetic spectrum.

In one embodiment the illumination sources contain elements for further light conditioning utilising refractive or reflective or dispersive optics such as lenses, beam splitters, planar or curved mirrors, filters, reflective or transmissive diffusers.

In one embodiment the device is provided with an interchangeable imaging lens system. The interchangeable imaging lens system can be integrated with an attachment enabling to maintain the optimal working distance between the imaging system and the inspected object.

In one embodiment the invention provides means for the automatic recognition of the imaging lens and removable attachment used. For example, bar code pattern within the field of view for the automatic recognition of the imaging lens and removable attachment can be used.

In one embodiment the optical system comprises one or more reflection pads for measuring variation of the intensities of illumination sources for further calibration.

In one embodiment a number of light sources are used simultaneously during the acquisition of a single image and a linear combination of the illumination vectors is used as a virtual source during the calculation.

In one embodiment the illumination sources comprise non-identical spectral characteristics to measure the spectral characteristics of the surface. The measured spectral characteristics can be used for colorimetry analysis of the skin tissue surface. The spectral characteristics can be measured using light sources of different wavelengths propagating to different depths below the surface and the spectral differences are used for the sub-surface characterisation of the surface.

In one embodiment the intensities of the illumination sources are calibrated using a reference surface with known shape and optical properties, and such calibration data is used during subsequent measurements to compensate for the variations of illumination intensities.

In one embodiment the variation in illumination properties for different points within the imaged area are taken into account to specify the surface properties for subsequent processing.

In one embodiment calibration data are acquired for each position within the viewing area and each illumination source to compensate for the errors due to changes of the illumination intensity.

In one embodiment the surface image captured is human skin tissue. Data collected can be used for the characterisation of human skin and the assessment of skin condition and health and/or for the identification of skin constituents present. The constituents can represent levels of oxyhaemoglobin, deoxyhaemoglobin melanin or collagen.

In one embodiment the device of the present invention is adapted for use in dermatology, skin care, aesthetic medicine, cosmetics or wound management applications such as the assessment of skin surface structure, and/or wrinkles analysis, and/or skin micro-relief and/or the examination of skin lesions and wounds.

In one embodiment there is provided a method of capturing images for the acquisition of the topography of a skin tissue surface, comprising:
  illuminating said surface using a plurality of illumination sources;
  capturing a plurality of images of said illuminated surface using an optical system;
  controlling said illumination sources and said optical system enabling changing spatial properties of the illumination and capturing said plurality of images with different spatial properties;
  eliminating specular reflection from said captured images; and
  analysing the differences between images captured with different illumination properties to reconstruct the topography of said surface based on a diffusive reflection model.

In a further embodiment there is provided an image capture device for the acquisition of the topography of a skin tissue surface, comprising:
  three or more illumination sources for illuminating said surface;
  an optical system adapted for the capture of a plurality of images of said surface;
  means for controlling said illumination sources and said optical system enabling changing spatial properties of the illumination and capturing said plurality of images with different spatial properties;
  means for eliminating specular reflection from said captured images;
  wherein two or more illumination sources are used simultaneously during the acquisition of a single image and a linear combination of representative illumination vectors is used as a virtual source, such that the two or more sources illuminate the surface at a time increases the illumination intensity and reduce the number of individual images acquired; and
  means for analysing the differences between images captured with different illumination properties to reconstruct the topography of said surface based on a diffusive reflection model to produce a three dimensional image of said skin tissue surface.

In another embodiment the invention relates to a method for assessing skin status in an individual, which method comprises a step of determining the concentration and/or distribution of one or more components in the individuals skin by employing the device of the invention, and correlating the concentration and/or distribution of the or each component with skin status. The term "skin status" should be taken to mean an assessment of the skin appearance; health of the skin when measured, or an assessment of risk that the skin is disposed to become unhealthy or diseased. In one preferred embodiment, the method is a method of assessing skin cancer status, for example whether the person has a skin cancer, or whether they are at risk of developing skin cancer. In this regard, the method typically involves determining or detecting an inhomogenous distribution of melanin and correlating the measured distribution with skin cancer status. Suitably, an inhomogenous distribution of melanin is determined by mapping a position, size, shape and/or colour of a mole in the individuals skin, or by detecting hyper pigmentation. In another embodiment, the method is a method of determining the status of a wound or lesion in the skin, for example, determining the status of a wound, especially chronic wounds, and determining the status of a vascular lesion, for example, a rosacea, acne or telengiactesia. In the case of wounds, and especially chronic wounds, the method of the invention is useful in monitoring chronic wounds for vascularisation, and thereby informing a physician as to the progress of healing, or the effectiveness of a specific treatment regime.

There is also provided a computer program comprising program instructions for causing a computer program to carry out the above method and control said device which may be embodied on a record medium, carrier signal or read-only memory.

BRIEF DESCRIPTION OF THE DRAWINGS

The invention will be more clearly understood from the following description of an embodiment thereof, given by way of example only, with reference to the accompanying drawings, in which.

DETAILED DESCRIPTION OF THE DRAWINGS

The present invention introduces a method and an apparatus for imaging the topography of skin or tissue surface in an accurate and reproducible way. To achieve this, the following specification describes methods for removing glare caused by specular reflection of light, which is the main source of errors in photometric stereo measurements. Also disclosed are methods to analyze tissue constituents and their distribution in the sub-surface layers. Furthermore, the apparatus which makes use of the described methods is described in detail with reference to the accompanying figures.

The invention relates to an optical device, system and/or apparatus for inspection of the topography and spectroscopic features of skin tissue. In the context of the invention the term 'tissue surface' encompasses images on the skin surface and surface layers below the skin tissue surface. The system comprises a case containing multiple light sources (e.g. light emitting diodes), means for focusing an image of the object (e.g. a lens) and an image sensor where an image of the object is formed (e.g. CCD or CMOS sensors). Additional elements, such as means for shaping the illumination (light condensers and/or diffusers), polarization filters and imaging apertures may also be used to optimize the configuration of the system. The device, apparatus and method of the invention facilitates three-dimensional imaging of partially diffusive and diffusive surfaces. They are based on multi-directional illumination and computer-aided reconstruction of the surface utilising the differences between images acquired from the specimen as a result of illuminations from different angles.

Figure 2:
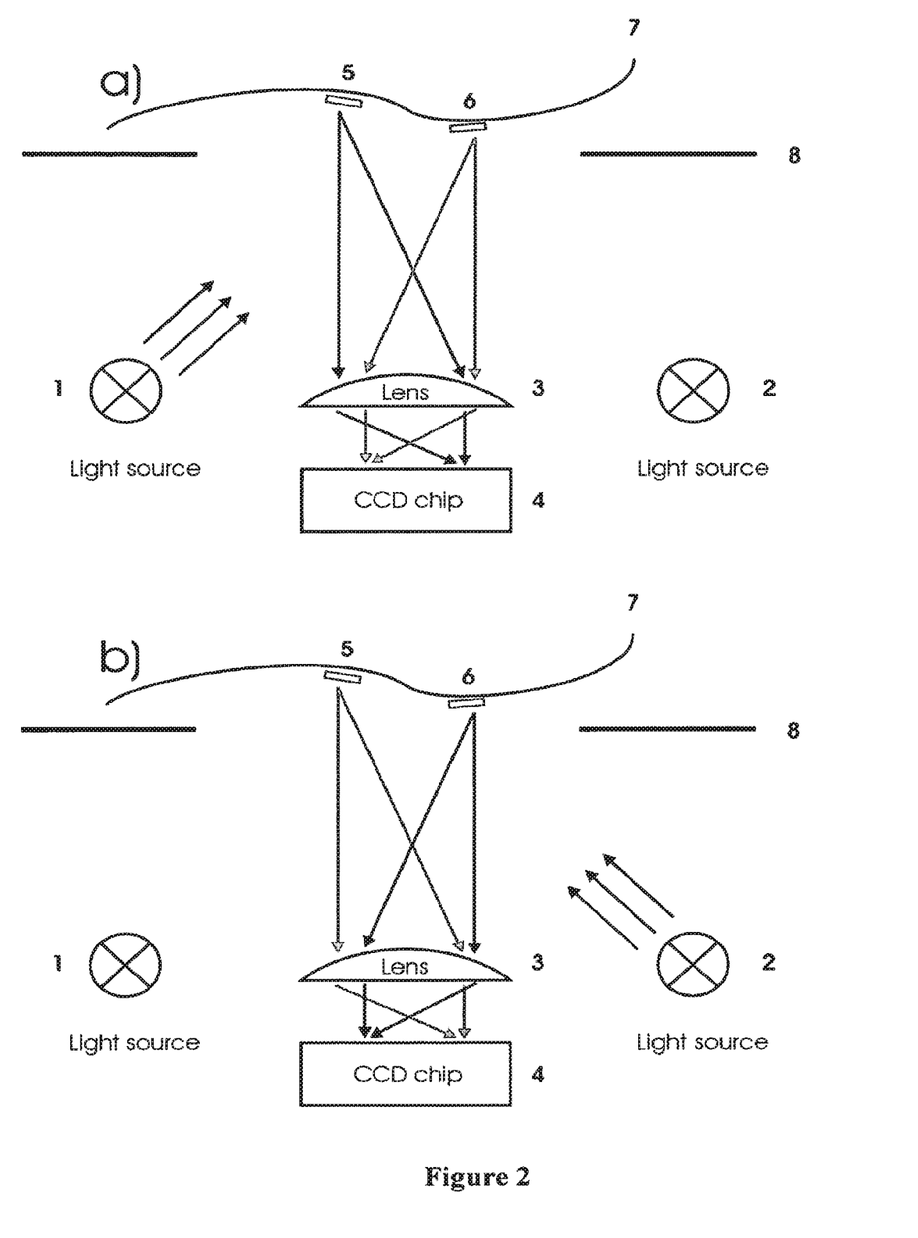
FIG. 2 illustrates the principle of surface shape imaging.

A schematic of the operating principle on which the invention is based is shown in FIG. 2. For the sake of clarity, only two sources are shown in the schematic, but the operating principle relies on the use of at least three illumination sources, and more sources can be used to increase the accuracy of the measurement. Two illumination sources can be used, however it will be appreciated that measurements will not be as accurate. FIGS. 2a and 2b show schematics of a surface of a sample (7) (e.g. a human skin surface) placed at the opening of a platen 8. Two areas of the sample surface, marked as (5) and (6), correspond to two pixels on an imaging sensor. The acquisition of the image takes place in a multiple step fashion, i.e. there are a number of acquisitions of subsequent images of the sample under different illumination conditions when different light sources are used to illuminate the sample. FIG. 2 shows the case of two light sources (1) and (2). In the first step, light source 1 illuminates the sample and light source (2) is switched off. In the second step the situation is reversed and the sample is illuminated by light source (2), while light source (1) is switched off. In both cases the reflected light passes through a lens (3) and is focused onto a CCD chip (4). Due to the geometry of the sample being analysed and the angle of incidence of the light, the detected intensities differ. For example, the intensity corresponding to the area (5) is higher for the first image than for the second one (FIG. 2a), while for the area (6) the situation is reversed (FIG. 2b). This is because the surface of area (5) is oriented facing more perpendicular towards source (1). The opposite situation holds for area (6), which is oriented facing more towards source (2). The differences in detected intensities under different illumination conditions can be evaluated by employing algorithms described below, and information about the geometry of the surface can thus be obtained. This translates into a three-dimensional reconstruction of the topography of the object.

It should be stressed that in relation to FIG. 2, when the light sources (1) and (2) were switched on in alteration one after another, it is implied that the intensity of the light produced by the sources was altered for each image taken. One could devise embodiment of the device where the light produced by the source (2) is not switched off completely when the source (1) is turned on and vice versa. Instead one could merely alter the intensity of the sources, e.g. the intensity of the source (2) is reduced by 90% when source (1) is fully on and vice versa. Nevertheless, knowing the value of the intensity changes one can still accurately evaluate the optical and shape properties of the tested surface.

The number of light sources does not need to be equal to three. To calculate the orientation of each individual area accurately, three or more light sources are required. One could also provide the apparatus with any other greater number of light sources and use regression analysis to increase accuracy of the measurement or eliminate data corresponding to least favorable illumination directions.

In the following, it is assumed Lambertian properties of the reflection of light from the surface of the object are present. The apparent light intensity at a particular position can then be determined as $I=r\,N\cdot D$, where N is the normalised vector perpendicular to the surface (surface normal), r is the optical reflection coefficient (reflectance) corresponding to the surface brightness and D is the illumination vector which is parallel to the illumination direction with magnitude proportional to the light intensity. The scalar product $N\cdot D$ depends on the cosine of the angle $\alpha$ between these vectors.

Using three light sources the illumination at particular position can be characterised by three numbers, given by illumination vectors $D_1$, $D_2$, $D_3$:

$$I_1 = r\,N \cdot D_1$$

$$I_2 = r\,N \cdot D_2$$

$$I_3 = r\,N \cdot D_3 \qquad (1)$$

These represent a system of three linear equations for three components of the vector N. The reflectance coefficient r can be isolated from the equations and the system has a to unique solution as long as $D_1$, $D_2$, $D_3$, are not parallel, which is guaranteed by the placement of the illumination sources. Once the surface vector N is known at each lateral point [x, y] of the image, the shape of the surface can be calculated in the form of surface elevation coordinate z as a function of the lateral coordinates x, y. This is usually performed by integration methods: the ratios $N_z/N_x$, $N_z/N_y$ of the vector N components represent partial derivatives of the surface function at a particular point, so that the difference in the z coordinates between two points A and B can be written in a form of a curve integral:

$$\Delta z = \int_c (N_z/N_x dx + N_z/N_y dy)$$

It is not necessary to restrict to any specific method or algorithm for solving the above integrals, these can be found in many mathematics textbooks. Here just one possible approach as an example as it is particularly suitable for applications of the present invention in skin tissue characterization.

An essential element of the present invention is the measurement of wrinkles of a skin tissue surface, and the fact that the calculation of the overall shape of the object, e.g. overall profile of the face and smooth features, is not required. These smooth features are characterised by low spatial frequencies in the Fourier spectrum. In contrast, one is interested in high frequency components of the Fourier spectrum representing sharp variations in the profile due to wrinkles. In this case, the calculation of the z coordinate for a particular position [x,y] can be simplified, as the curve integrals can be transformed to surface integrals over a limited area surrounding that position. This simplification assumes the continuous character of the surface without step-like discontinuities. The contribution from the surface tilt at surrounding position [x', y'] can then be expressed as a scalar product:

$$dz = P \cdot S$$

where a two-dimensional contribution vector $P = [N_z/N_x, N_z/N_y]$ (where $N_x$, $N_y$ and $N_z$ are components of the normalised vector N) represents the influence of the tilt on the z coordinate change, and S is a normalised position vector between the points [x, y] and [x', y'] multiplied by a normalised distribution function. For our purposes, normal distribution function can be chosen and the vector S calculated as:

$$S = [(x-x')/d, (y-y')/d] \cdot 1/\sqrt{(2\pi)} \cdot \exp(d^{-2}/2)$$

where $d = \sqrt{(x-y')^2 + (y-y')^2}$ is the distance between inspected and contribution points. The elevation coordinate z for each point [x, y] can be finally calculated as:

$$z = \int_A P \cdot S$$

where the integration area A surrounding the inspected point [x, y] can be limited to a distance for which $1/\sqrt{(2\pi)} \int_A \exp(d^{-2}/2) \, dx \, dy$ is close to 1.

Figure 3:
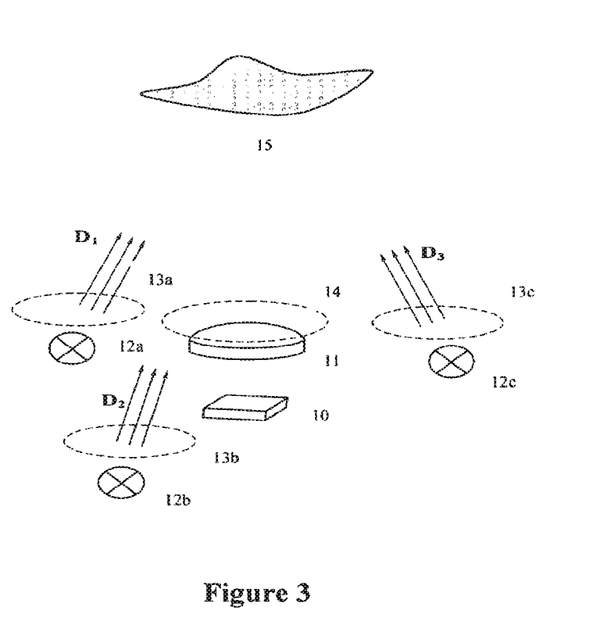
FIG. 3 illustrates a configuration of the device according to one aspect of the present invention.

One of the preferred embodiments of the apparatus according to the invention is shown in FIG. 3, The invention comprises a single camera (10), for example a CCD or CMOS sensor, with an imaging optics (11), collimating optics 14 and three illumination sources (usually LEDs) (12a), (12b) and (12c). Illumination sources (12a), (12b) and (12c) are coupled with linear polarisation filters, (13a, 13b, 13c). Linear polarisation filters are positioned with polarisation perpendicular to that of collimating optics (14), a surface (15) of an object to be inspected, for example skin tissue. During the measurement process, each pixel of a given image is illuminated from three different directions by three light sources. These sources are controlled by an electronic strobing system synchronised with the frames grabbed by the camera. As each pixel in the camera corresponds to a particular lateral position on the object surface, the differences between the intensities acquired from different illumination angles depend on the particular tilt of the surface. Based on these differences, the normal vector can be evaluated for each position within the area of interest and the overall shape of the object can be calculated and reconstructed using integration methods.

Reflection from tissue is a combination of diffusive and specular reflections. Specular reflections can be very intense and can make topographical features of a surface impossible to evaluate. The diffusive Lambertian reflection, used in the above described calculations, does not account for specular reflection. This means that to calculate accurately the shape of the surface one needs to eliminate specular reflections. The elimination of the specular reflection is one of the main advantages of the present invention.

According to the invention, the first method to suppress the glare during 3D surface acquisition is a method where cross-polarisation is employed. The use of polarised light is common in the fields like microscopy and polarisation dependent imaging. For the elimination of specular reflection for 3D acquisition the invention takes advantage of a particular property of light reflection. The light specularly reflected from a tissue surface does not change its polarization state, while light that undergoes diffusive reflection can change its polarisation state, see for example 'Lawrence B. Wolff and Terrance E. Boult, IEEE Trans. Patt. Analysis, 13 (1991) 635-657'. To eliminate the contribution of the former, cross-polarised filters (13a), (13b) and (13c) are used in front of the light emitting sources (12a), (12b), (12c), which allow transmission of the light only for one polarisation state (A), while placing a polarization filter (14) for orthogonal polarisation state (B) in front of the imaging optics (11). In a preferred embodiment, linear polarisation filters are used with polarisation direction of filter (14) rotated by 90 degrees relative to the common direction of filters (13a), (13b) and (13c). It has to be noted that the filters for other orthogonal polarisation states, the right and left circular polarisers, can be used instead of the linear polarisers for certain surfaces, although the use of such polarisers can be more expensive and more prone to variations of the properties with respect to the light wavelength.

For another embodiment of the present invention to further suppress the specular glare, the polarisation method can be combined with removal of redundant data with residual specular component in multi-illumination configuration. Such a method, is based on the fact that although the specular reflection is significantly stronger than the diffusive one, such reflected component has strong directionality and its intensity decays quickly for directions deviating from the one corresponding to the law of regular reflection. This means that for a particular point on the surface and a particular observation direction (represented by the vector towards the imaging sensor) the specular reflection can be observed only in the case when the illumination direction is close to fulfill the law of to regular reflection. If the directions of the illumination sources differ substantially with respect to the surface, specular reflection is at a maximum for one source and one particular direction. By using more illumination sources with different illumination directions, the redundant data (corresponding to specular reflection and maximum detected intensity) can be discarded. The identification and elimination of specular reflection is performed independently for each point of the surface. This means that for example the discarded data with maximum specular reflection for one pixel can correspond to data acquired first image and for another pixel do data within second image. Each pixel is assessed individually with different set of data. By repeating this procedure for each pixel of the camera, data burden by specular reflection can be eliminated and the surface can be accurately evaluated.

In one of the preferred embodiments, four LED sources are used and four images are acquired for different sources switched. For each position within the image (e.g. each individual pixel), the acquired intensities for all illuminations are evaluated and compared and the data corresponding to specular reflection most closely (with highest intensity level) is discarded from the calculation which comprise the data only for the other three illuminations. One can also use a higher number of illuminations to eliminate one or a group of data with least favorable illumination, not necessarily corresponding only to specular reflection but also, for example, data corresponding to a shadowing effect when an area is obscured from particular illumination source by another part of the object imaged (common for surfaces with step-like features). In this case such data can be specified by the lowest intensity level. The rest of the data can be then used for the shape calculation, in a case that this number is greater than three, and a regression analysis can be applied.

Figure 4:
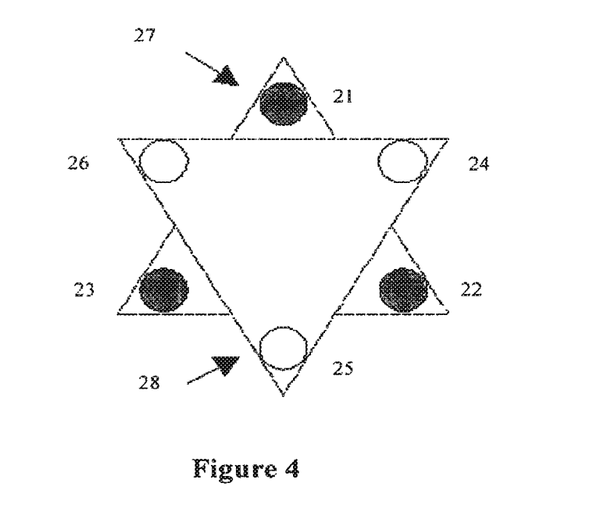
FIG. 4 is a top view of the schematic of two LED circuits according to a further aspect of the present invention.

In another embodiment of the invention six light illumination sources (e.g. LEDs) are used, indicated by the reference numeral (21) to (26) as shown in FIG. 4. In order to use the same data evaluation method for three sources as described above and simplify the algorithm for image reconstruction, the six LEDs can be grouped into two separate circuits, (27) and (28), each containing three LEDs. The LEDs (21), (22) and (23) of circuit (27) are positioned at 120 degrees with respect to each other, and so are the LEDs (24), (25) and (26) of circuit (28). The LEDs of circuit (27) are positioned at 60 degrees with respect to the LEDs of circuit (28). The two circuits (27) and (28) are controlled by an electronic strobing system synchronized with the camera of FIG. 2. LED (21) is switched on to illuminate the tissue. Once it has been switched off, LEDs (22) and (23) follow in sequence. Likewise the same approach is used for LEDs (24), (25) and (26) of circuit (28). Again the intensities of the light reflected can be compared for each point of the sample and the higher one, corresponding to the greatest contribution of specularly reflected light, can be discarded.

It should be noted that the two methods described above to suppress specular reflection can be combined, which would be very advantageous for highly specular surfaces. One can also devise a system where the direction of the source and the direction of the imaging system are used to calculate the orientation of the surface that corresponds to high specular reflection.

A further embodiment of the invention provides a calibration process for eliminating the errors caused by non-uniform illumination. The acquisition methods described above rely on the assumption that both the illumination direction and intensity are known. Common assumption in photometric stereo methods is uniform illumination intensity through the whole field of view. However, in practice this is not always the case especially for large surfaces and relative close proximity of the illumination source to the surface. Both the direction and intensity of illumination can differ from point to point of the viewed area due to the different position relative to the illumination source and inhomogeneous radiation pattern of the sources. To remedy this problem, the illumination properties are measured individually for each position and each illumination source and stored for later data processing.

The illumination direction can be determined from the geometric configuration of the system. If no focusing optics is used between the sources and the particular position within the field of view, the direction can be determined just as a relative position vector between given point and the position of the source. In a case when focusing optics is used to shape the light beam, the direction can be determined as relative position vector between given point and position of the virtual source. The virtual source is determined as the optical image of the source through said focusing optics.

The light intensity level is more difficult to determine as it depends on the particular properties of the light source and can differ significantly for particular illumination element. To determine the light intensities calculations can be based on measurements performed on well defined samples with known geometry and reflectivity coefficients. In preferred configuration a flat surface of material with well defined uniform optical properties, such as Spectralon or Teflon can be used. These materials have flat reflectance spectra with reflectivity values close to 1 in the visible range.

Measured reflectance intensities can be then compared to the theoretical values based on Lambertian reflectance model with respect to the position of illumination and particular position of within the image data for each pixel of the image. In such a way the real light intensity levels at particular position within the field of view can be determined, these values can be stored within the computer memory system (and the disk) and used later as a normalisation coefficients during normal image acquisition on samples with unknown properties.

A particularly convenient form of representing lighting conditions is the use of an illumination vector at each position within the measured area corresponding to each pixel of the imaging detector. Such illumination vector is parallel to the direction between illumination source and the particular position within the field of view and its magnitude is proportional to the light intensity at that point. For each illumination source the calibration data forms a set of such vectors (with the number corresponding to the number of pixels within the detector), which are marked as D vectors in equation (1) above.

It should be noted that the light intensities of the illumination sources might vary in time. As far as LEDs are concerned, this is usually caused by the change of the temperature at P/N junction and corresponding decrease of the LEDs light emission efficiency and variation of the light intensities when the system is used for an extensive period of time. With high degree of accuracy, these changes can be corrected with a single multiplication factor which would be applied to all calibration vectors D at given acquisition time. This single efficiency factor can be used thanks to the fact that the relative spatial distribution of the light depends mostly on the LED emitter geometry which does not change in time. The time variation of the intensity and said factor can be determined either by a separate sensor measuring overall intensities of the emitted light or by the imaging sensor itself. According to another invention, a special reference target with well defined optical reflectance is located in the proximity of the viewed area.

Figure 5:
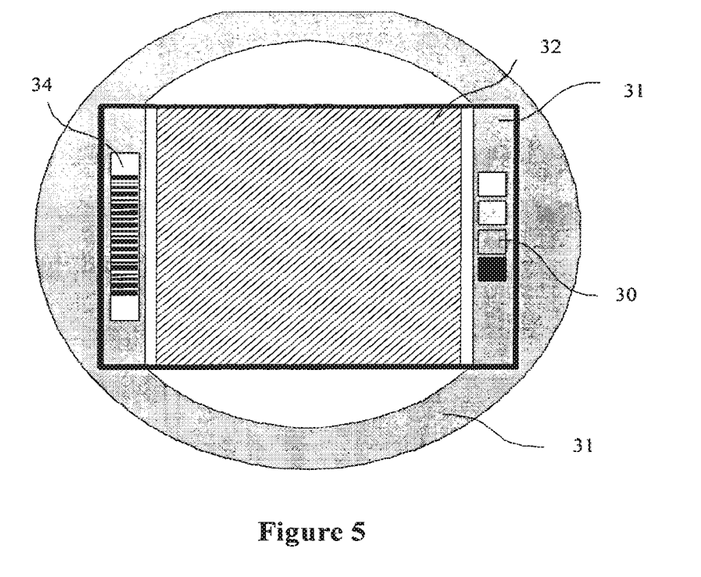
FIG. 5 illustrates calibration of illumination intensity of the device according to another aspect of the present invention.

FIG. 5 shows the field of view from the perspective of the camera imaging system for the calibration of illumination intensity. Reference target area (30), attached to the nozzle (31), lie close to the edge of a sensor active area (32). Only subset of this area, shaded area (32), is used for the imaging of the surface of inspected object. Other parts of the area (32), lying outside sensor active area (32), can be used e.g. for recognition of the used attachment and lenses (34). The measured data from the reference targets determine the multiplication factor to calibrate the illumination intensities every time a new set of images is taken. The target can consist of several areas with different brightness to avoid under exposure or saturation at the imaging sensor when different exposition regimes of the sensor have to be used to accommodate accurate imaging of surfaces with different overall brightness. As particular target areas can lie within many pixels of the imaging sensor, a sum of intensities over that target or its average value can be used as a calibration factor for the illumination intensity to increase the accuracy of the measurement.

Figure 6:
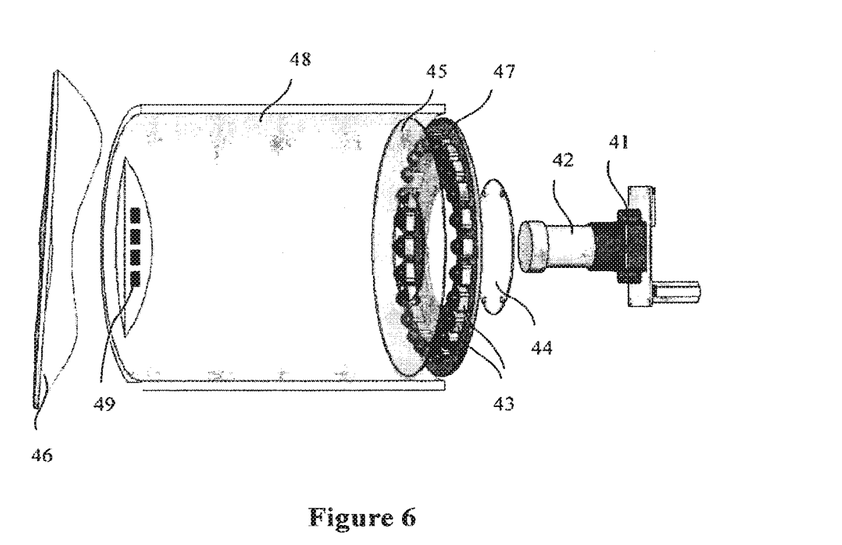
FIG. 6 is a 3D perspective assembly view of the imaging device according to the present invention.

FIG. 6 shows an example configuration of the apparatus/device according to the invention. It consists of an imaging sensor and acquisition system (41), for example a PointGey Firefly MV camera, an imaging lens (42), for example a 10 mm focal length micro-video lens, a PCB board (47) with electronic control to control a plurality LED light sources (43), for example Luxeon K2 emitters, a polarisation ring (45) positioned in front of the light sources and polarisation filter positioned in front of the imaging lens (44). In front of the imaging system, the device is provided with a nozzle (48) to limit the influence of external background illumination and to control the distance of the surface of an inspected object surface (46). Optional calibration targets (49) can measure the overall light intensities and to eliminate its variation as described above.

Figure 7A:
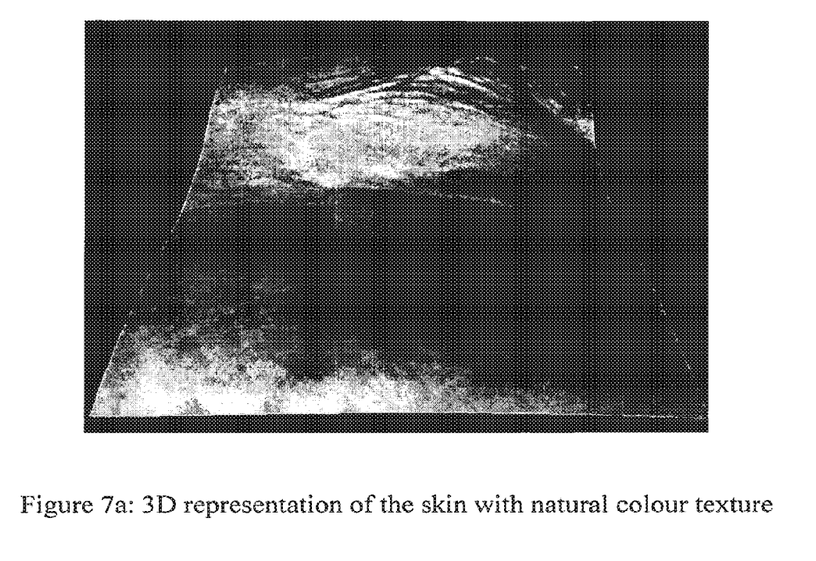
FIG. 7a-e illustrates 3D representations of images of a skin surface captured by the device according to the present invention.
Figure 7B:
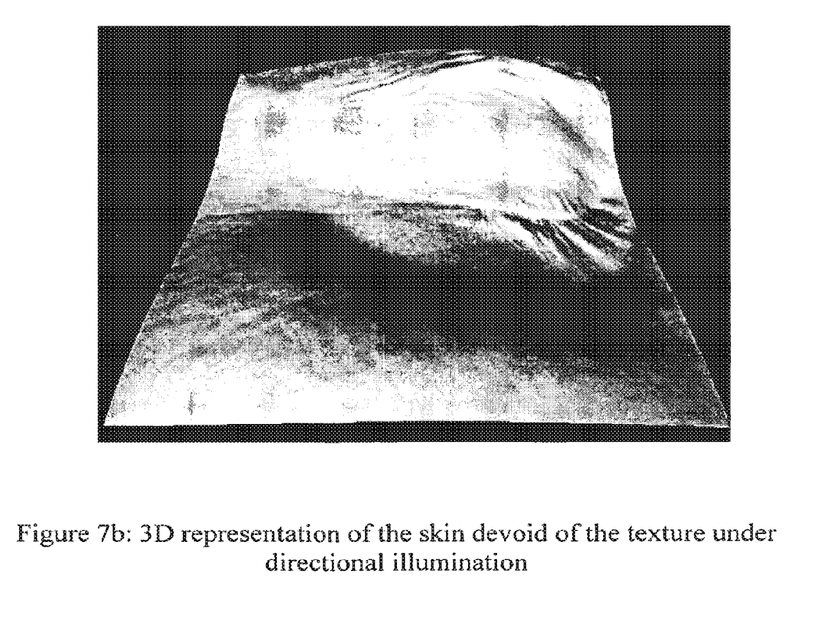

FIG. 7a shows 3D representation of real measured topography of a facial skin surface showing a human eye, according to the present invention. The shape is visualised by the use of a virtual lighting and shadows caused by its directionality. An alternative representation, with a false color mapping of z elevation for each x, y coordinate, is shown in FIG. 7b. In this image virtual lighting is still used to express small variations of the surface shape.

Based on the data acquired by the imaging sensor it is possible to evaluate not only the shape of the inspected object, but also the reflectance of the surface for the lights used.

Figure 7C:
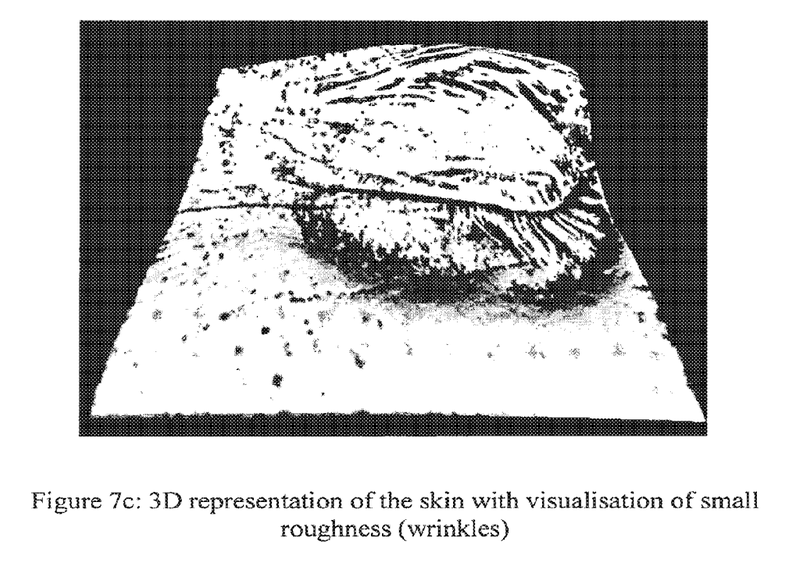

Once the surface normal vector N is determined, the surface reflectance can be calculated as r=I/N·D), where I is the measured intensity, N is the surface normal and D is the vector representing the illumination source. This source can be either one used for the acquisition of the surface shape or it could be a different one having different wavelength. Using various sources with different wavelengths allows acquisition of extensive spectral reflectance data. Knowing the shape of the surface the influence on the illumination direction can be removed and true optical properties can be evaluated. This represents a significant advantage over images obtained in conventional ways and such images are much more suitable for quantitative and comparative evaluations due to their independence on the lighting conditions. Although this spectral data can be used to synthesize normal colour appearance of the surface, as illustrated in FIG. 7c, the independence on lighting conditions can be used for additional analysis of the properties of the imaged object. Additionally, it will be appreciated that richer spectral data can be acquired, as opposite to the three channels Red, Green and Blue (RGB) used for standard colour imaging, which allows a better characterisation of the object.

In the specification it is assumed that light is scattered on the surface boundary. For some materials, such as skin, light can propagate to a certain depth below the surface before it is scattered back. This propagation is characterised by an average value, called depth of propagation, which usually strongly depends on the light wavelength. For example, light of greater wavelength propagates deeper below the surface. This realization allows the invention to investigate the distribution of various constituents of biological tissue below the surface boundary. In the preferred embodiment of the invention, light sources of several different wavelength are used. The light sources can span the electromagnetic spectrum from the infrared to the ultraviolet end.

The present invention makes use of a plurality of Luxeon K2 LED emitters with dominant wavelengths of 455, 470, 505, 530, 590, 617 and 627 nm. It will be appreciated that light sources outside the visible range can also be used to obtain additional information about the sample properties. Since the penetration depth increases as a function of the wavelength, ultraviolet or blue light is more suited to obtain information on the outermost layer of the tissue, while radiation closer to the infrared end of the spectrum will carry information about deeper layers of skin tissue. Multi-spectral imaging of various constituents of skin tissue below the surface can be achieved by using a number of light sources that span the electromagnetic spectrum in the desired range.

For example, the reflectance spectra measured by the present invention can be correlated to the absorption spectra of skin constituents. The measured values of melanin and haemoglobin, the two main chromophores of human skin, can be compared to the theoretical values obtained using an optical model of skin reflection. Depending on the type of skin and illumination, various models of the reflection can be used to analyse the acquired data.

The more accurate models of light propagation in the skin are based on Monte-Carlo iteration methods, for example as disclosed by Robert Splinter, Brett A. Hooper, An Introduction to Biomedical Optics, Taylor & Francis, London 2006, ISBN: 9780750309387, pp. 182 and Scattering and absorption of turbid materials determined from reflection measurements. 1: Theory; R. A. J. Groenhuis, H. A. Ferwerda, and J. J. Ten Bosch; Applied Optics, Vol. 22, Issue 16, pp. 2456-2462. However, these methods require substantial computational resources requiring a long time for data analysis. The results of simpler methods making use of regression analysis are usually burden with larger errors but they have the advantage of being much faster as they are based on simplified, but explicit, equations of the reflection, using known absorption and scattering coefficients of the skin constituents, see for example R. R. Anderson and J. A. Parrish. The optics of human skin. Journal of Investigative Dermatology, 77 (1981), pp. 13-19.

The measured reflectance data model has to take into account the directionality and the particular spectrum of the light used. Using the device of the present invention the exact placement of the illumination sources and the shape of the imaged skin surface are known makes it possible to recalculate the reflection coefficients under homogeneous illumination for each wavelength and for each pixel. By eliminating the specular component of reflected light, it is possible to use the Lambertian reflection model and the same equations, as described above, for calculating accurate reflection coefficients. Furthermore, the elimination of specular reflection suppresses the effect of undesired specular reflection from the stratuum corneum.

Isotropic light propagation in the epidermis and dermis then permits the use of the relatively simple Kubelka-Munk light propagation model, see for example P. Kubelka: New contributions to the optics of intensely light materials; J. Opt. Soc. Am. 44(1954), pp. 330-335, and allows the invention to correlate the measured data with the concentration of melanin and haemoglobin, see for example T. J Farrell, M. S Patterson, B. Wilson: A diffusion theory of spatially resolved, steady-state diffuse reflectance for the non-invasive determination of tissue optical properties in vivo; Med. Phys. 19 (4), pp. 879-888.

The concentration and distribution of skin constituents has important implications in the assessment of skin health and the diagnosis of a number of conditions in the context of the present invention. For instance, hyper pigmentation caused by prolonged sun exposure can be easily identified and an inhomogeneous distribution of melanin on a particular area can be interpreted as a precursor of skin cancer. This opens up applications for the present invention as a potential skin cancer screening tool by accurately mapping moles position, size, shape and colour and tracking their evolution over time. Thus, the invention provides a diagnosis method and device to detect indicators that a patient is prone to skin cancer.

The ability to measure the distribution of haemoglobin, the main chromophore of human blood, can be used to examine a number of vascular lesions, e.g. rosacea, acne and telengiactesia. In the field of wound care for patients, where treatments of chronic wounds can take up to several months and the efficacy of a given treatment is often unclear, the measurement of the vascularisation of the wound can help the physicians in identifying the most appropriate treatments and to shorten the healing time. Thus, the invention provides a diagnosis method and device to detect indicators to determine the status of a patients wound.

Figure 7D:
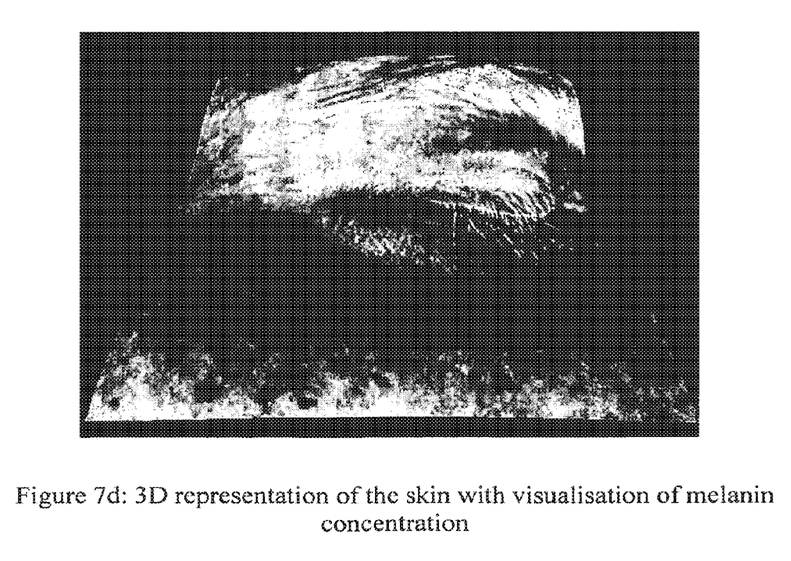
Figure 7E:
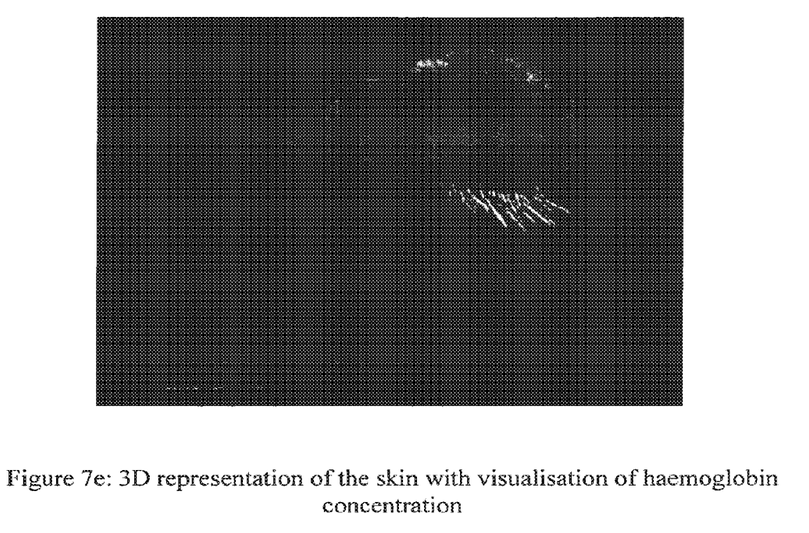

FIGS. 7d and 7e show the distributions of melanin and hemoglobin based on in-vivo spectral measurements acquired by the device of the present invention.

To allow the change of the magnification and field of view of the imaging apparatus/system of the present invention, the apparatus can comprise either a zooming system with a single lens that has variable focal length or a lens-exchange system with a set of lenses of fixed focal length. The latter system is less costly and is the one used in one of the preferred embodiments described above. For the acquisition of high resolution images it is essential to keep the working distance from the object within a certain range acceptable for the lenses. To accommodate this, the imaging system can be equipped with a removable attachment. Because each lens has a different working distance, each lens will be integrated in a different removable attachment. To determine which attachment is mounted and which calibration data should be used for the evaluation of the images, the apparatus of the present invention can be equipped with an attachment-recognition system. This can be performed either by using a sensor (electric, optical or magnetic) or by attaching a special pattern to the removable attachment within the viewing field of the imaging system. The pattern itself can be either in the form of a bar-code strip reader, for example a bar-code commonly used for recognition of consumer goods and products, and shown as element (34) in FIG. 5. Alternatively a color-encoded or other pattern can be used which can be easily processed by the imaging system. Because the intensities and spatial positions of the illumination sources will be different depending on what attachment is used, the use of different calibration data (described in previous part of the specification) will be required.

The embodiments in the invention described with reference to the drawings comprise a computer apparatus and/or processes can be performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments herein before described but may be varied in both construction and detail.

The invention claimed is:

1. An image capture device for the acquisition of the topography of a skin tissue surface, comprising:
   a plurality of illumination sources for illuminating said surface;
   an optical imaging system adapted for the capture of a plurality of images of said surface;
   a controller for controlling said illumination sources and said optical system enabling changing the illumination directions and capturing said plurality of images with different spatial properties,
   wherein during the acquisition of at least one image the plurality of individual illumination sources illuminate the surface simultaneously,
   wherein properties of the plurality of simultaneously illuminating sources are characterised to a single virtual source based on a calibration obtained from the illumination properties measured individually for each position and each illumination source previously,
   at least two polarisers for eliminating specular reflection from said captured images, a first polariser positioned between the illumination sources and the surface, and a second polariser between the surface and the optical imaging system; and
   a processor for analysing the differences between images captured with different illumination properties to reconstruct the topography of said surface based on a diffusive reflection model to produce a three dimensional image of said skin tissue surface,
   wherein the variation in illumination properties for different points within the imaged area are taken into account to specify the surface properties for subsequent processing,
   wherein data for each image and position are adjusted according to prior calibration data to compensate for the errors due to variations in the illumination intensity or in the illumination direction,
   wherein said calibration data characterize the effective intensities and directions of the illumination sources for each image and position within the viewing area, and
   wherein said prior calibration data were obtained from calibration images using a reference surface with known shape and optical properties, and such calibration data is used during subsequent measurements.

2. The image capture device according to claim 1 wherein the first and second polarisers are linear light polarisers and aligned in a cross-polarised relationship with each other.

3. The image capture device according to claim 2 wherein the plurality of captured images are of substantially the same area with varying illumination conditions all under the same polarisation direction of the incident light and substantially cross-polarised direction of detected reflected and scattered light.

4. The image capture device according to claim 1 wherein the means for analysing comprises processing said plurality of captured images to calculate the tilt of the surface at each point of the area from the difference between images taken under different illumination conditions and recover the topography of the surface.

5. The image capture device according to claim 1 wherein at least one of the illumination sources operates within the visible range of electromagnetic spectrum.

6. The image capture device according to claim 1 wherein at least one of the illumination sources emits radiation outside the visible range of the electromagnetic spectrum.

7. The image capture device according to claim 1 wherein the illumination sources contain elements for further light conditioning utilising refractive or reflective or dispersive optics such as lenses, beam splitters, planar or curved mirrors, filters, reflective or transmissive diffusers.

8. The image capture device according to claim 1 comprising an interchangeable imaging lens system.

9. The image capture device according to claim 8 wherein the interchangeable imaging lens system is integrated with an attachment to maintain the optimal working distance between the imaging system and the inspected object.

10. The image capture device according to claim 8 comprising means for the automatic recognition of the imaging lens and removable attachment used.

11. The skin tissue image capture device according to claim 8 comprising within the field of view specific patterns such as bar code patterns and colour-coded patterns specific for each of the imaging lens and removable attachment, and used for their automatic recognition.

12. The image capture device according to claim 1 wherein the optical system comprises one or more reflection pads for measuring variation of the intensities of illumination sources for further calibration.

13. The image capture device according to claim 1 wherein said illumination sources comprise non-identical spectral characteristics to measure the spectral characteristics of the surface.

14. The image capture device according to claim 13 wherein the measured spectral characteristics are used for colorimetry analysis of the skin tissue surface.

15. The image capture device according to claim 13 wherein the spectral characteristics are measured using light sources of different wavelengths propagating to different depths below the surface and the spectral differences are used for the sub-surface characterisation of the surface.

16. The image capture device according to claim 1 wherein the surface image captured is human skin tissue.

17. The image capture device according to claim 16 wherein data collected is used for the characterisation of human skin and the assessment of skin condition and health and/or for the identification of skin constituents present.

18. The image capture device according to claim 17 wherein said constituents represent levels of haemoglobin, oxyhaemoglobin, deoxyhaemoglobin, melanin or collagen.

19. The image capture device according to claim 1 wherein the image is human skin tissue.

20. The image capture device according to claim 1 wherein the image is related to skin lesions and wounds of human skin tissue.

21. A method of capturing images for the acquisition of the topography of a skin tissue surface, comprising the steps of:
    illuminating said surface using a plurality of illumination sources;
    capturing a plurality of images of said illuminated surface using an optical system;
    controlling said illumination sources and said optical system enabling changing spatial properties of the illumination and capturing said plurality of images with different illumination directions, wherein during the acquisition of at least one image the plurality of individual illumination sources illuminate the surface simultaneously, wherein properties of the plurality of simultaneously illuminating sources are characterised to a single virtual source based on a calibration obtained from the illumination properties measured individually for each position and each illumination source previously, wherein the intensities of the illumination sources are calibrated using a reference surface with known shape and optical properties, and such calibration data is used during subsequent measurements to compensate for the variations of illumination intensities;
    eliminating specular reflection from said captured images; and
    analysing the differences between images captured with different illumination properties to reconstruct the topography of said surface based on a diffusive reflection model,
    wherein the variation in illumination properties for different points within the imaged area are taken into account to specify the surface properties for subsequent processing, and
    wherein calibration data is acquired for each position within the viewing area and each illumination source to compensate for the errors due to variations in the illumination intensity or in the illumination direction.

22. The image capture device according to claim 1, further comprising means for calibrating each individual source based on a measurement of light intensity for each individual pixel within a device field of view and measured upon response over a well-defined target reference surface, and the property of the characterized virtual source is determined as a sum of vectors of individual sources, and wherein a magnitude of each individual source is proportional to its illumination intensity, and the direction of each individual source is determined as normalised positional difference between pixel coordinates and the source coordinates.

* * * * *